United States Patent [19]
Forssmann

[11] Patent Number: 4,751,284
[45] Date of Patent: Jun. 14, 1988

[54] CARDIODILATIN, A NEW PEPTIDE HORMONE AND PROCESS FOR ITS PREPARATION

[75] Inventor: Wolf-Georg Forssmann, Heidelberg, Fed. Rep. of Germany

[73] Assignee: Organogen Medizinisch-Molekularbiologische Forschungsgesellschaft m.b.H, Heidelberg, Fed. Rep. of Germany

[21] Appl. No.: 769,627

[22] PCT Filed: Dec. 21, 1984

[86] PCT No.: PCT/DE84/00279
§ 371 Date: Aug. 20, 1985
§ 102(e) Date: Aug. 20, 1985

[87] PCT Pub. No.: WO85/02850
PCT Pub. Date: Jul. 4, 1985

[30] Foreign Application Priority Data
Dec. 24, 1983 [DE] Fed. Rep. of Germany ....... 3346953

[51] Int. Cl.⁴ .................... C07K 7/10; A61K 37/02; A61K 49/00
[52] U.S. Cl. ................................ 530/329; 530/326; 530/327; 530/328; 530/329; 530/350; 530/399; 530/841
[58] Field of Search ............... 530/324, 326, 327, 328, 530/329, 350, 399, 841

[56] References Cited
U.S. PATENT DOCUMENTS
4,604,234 8/1986 Fujii et al. .................... 530/350
4,638,050 1/1987 Aoki et al. .................... 530/350
4,675,382 6/1987 Murphy ....................... 530/350

FOREIGN PATENT DOCUMENTS
0159943 10/1985 European Pat. Off. .

OTHER PUBLICATIONS
Forssmann et al, "The Right Auricle of the Heart is an Endocrine Organ", *Anatomy and Embryology* (1983) 168:307–313.
Lazure et al, FEBS Letters, vol. 172, No. 1, pp. 80–86, "Atrial Pronatriodilatin: A Precursor for Natriuretic Factor and Cardiodilatin".
Nakayama et al, *Nature*, vol. 310, No. 3979, pp. 699–701, "mRNA Sequence for Human Cardiodilatin–Atrial Natriuretic Factor Precursor and Regulation of Precursor mRNA in Fat Atria".

*Primary Examiner*—Delbert R. Phillips
*Assistant Examiner*—Nathan M. Nutter
*Attorney, Agent, or Firm*—Felfe & Lynch

[57] ABSTRACT

There is described a new peptide hormone (cardiodilatin) and a process for its preparation, with the amino acid sequence: Asn-Pro-Val-Tyr-Gly-Ser-Val-Ser-Asn-Ala-Asp-Leu-Met-Asp-Phe-Lys-Asn-Leu-Leu-Asp-His-Leu-Glu-Asp-Lys-Met-Pro-Leu-Glu-Asp-Glu-Ala-Met-Pro-Pro-Gln-Val-Leu-Ser-Glu-Gln-Asp-Glu-Glu-Val-Gly-Ala-Pro-Leu-Pro-Leu-Leu-Glu-Glu-Val-Pro-Pro-Trp-Thr-Gly-Glu-Val-A n-Pro of the composition Asp/Asn 14, Thr 3, Ser 15, Glu/Gln 12, Pro 10, Gly 12, Ala 10, Val 7, Met 4, Ile 1, Leu 15, Tyr 2, Phe 3, Lys 4, His 2, Arg 10, Trp 2, a molecular weight of 13000 Dalton and an isoelectric point I.P. of 6 to 6.5.

The peptide hormone, as well as its C-terminal fragments obtained after partial cyanogen bromide fission between and behind Met groups, possess a high relaxing action on the smooth bloodvessel musculature.

30 Claims, 11 Drawing Sheets

FIG. I

Run #4  Pool 4  Sep G 75 (8,9,10,11,83)  25 mg
dissolved in  μl 0.1 % TFA  (5×10 μC for Bioassay)
05-12-83  —  280 nm / 2.0 AUFS
0.2 Volt CARDIODILATIN – Fragment
    Lys-Lys-(1-7)
Retentionszeit : 35,8 Min.
Gradient : A (0,1% TFA in H$_2$O)
          B (0,1% TFA in Methanol)
Min. 0-10 (100%A), Min. 11-40 (0-50% B)

```
INJECT 22:28:49 1
          315
                            358
                   388
             418
          428
             448
          475

NO OF RUN  23:20:51
HPVY (G,A) SV
NO:1
  EINZEL    JAN-25-00  22:28

FLOW RATE  : 1,3
FLOW MODE  : QG
TEMPERATURE: 25
PRESSURE   : 0117
COLUMN     : LATEK 250 X 4 GA 89.P-5

CHAN 1        : 200
MOBILE PHASE FILE 3
 TIME   %A    %B
       100.0   0.0
       100.0   0.0
        50.0  50.0
        50.0  50.0
       100.0   0.0
       100.0   0.0
```

INJECT 10:29:25 1

CARDIODILATIN-Fragment
(1-7) Variant Met (Pos.3),
Asn (Pos.5), Ala (Pos.6)
Retention time : 35,5 Min.
Gradient : A (0,1% TFA in H2O),
B (0,1% TFA in Methanol)
Min. 0-5 (100%A), Min. 5-35
(0-40%B)

END OF RUN    11:09:28

IPMYNAY

FLOW RATE : 1,0
FLOW MODE : QG
PRESSURE  : 0042
COLUMN : HD-SIL-18-5S-100 H
CHAN 1 : 200
CHAN 2 :
MOBILE PHASE H2O-MEOH (0,1% TFA)
MOBILE PHASE FILE 3

| TIME | %A | %B |
|---|---|---|
| 0.0 | 100.0 | 0.0 |
| 5.0 | 100.0 | 0.0 |
| 35.0 | 60.0 | 40.0 |
| 40.0 | 100.0 | 0.0 |

END OF PROGRAMMED RUN

JUL-30-84  10:29

CHANNEL 1   RUN 47   FILE 1   METHOD
INDEX 22

| PEAK | AREA% | RT | AREA |
|---|---|---|---|
| 1 | 582 | 283 | 1549 |
| 2 | 12.81 | 316 | 34069 |
| 3 | 86.61 | 355 | 230393 |
| TOTALS | 99.99 | | 266011 |

INJECT 08:01:11 1

CARDIODILATIN - Fragment
(8-19)
Retention time : 26,8 Min.
Gradient : A (0,1% TFA in H₂O)
B (0.1% TFA in Methanol)
Min. 0-10 (100%A), Min. 10-60
(0-40%B)

END OF RUN   09:06:14

END OF PROGRAMMED RUN   SNADLMDFKNLL

FLOW RATE    : 1,0
FLOW MODE    : QG
TEMPERATURE  : 35
PRESSURE     : 0088
COLUMN       : HD-SIL-18-5S-100N

CHAN 1       : 254
MOBILE PHASE : H2O METHANOL
MOBILE PHASE FILE 4

| TIME | %A    | %B   |
|------|-------|------|
| 0.0  | 100.0 | 0.0  |
| 5.0  | 100.0 | 0.0  |
| 35.0 | 60.0  | 40.0 |
| 40.0 | 100.0 | 0.0  |

| PEAK | AREA% | RT | AREA |
|------|-------|-----|---------|
| 1 | 1,951 | 63 | 72567 |
| 2 | 1,668 | 91 | 62051 |
| 3 | 318 | 170 | 11844 |
| 4 | 801 | 251 | 21 |
| 5 | 91,97 | 268 | 3421112 |
| 6 | 339 | 310 | 12598 |
| 7 | 1,067 | 378 | 39678 |
| 8 | 199 | 415 | 7391 |
| 9 | 1,772 | 525 | 65931 |
| 10 | 432 | 618 | 16067 |
| 11 | 313 | 635 | 11665 |
| TOTALS | 100 | | 3720925 |

CARDIODILATIN - Fragment
(38-44)
Retention time : 25,9 Min.
Gradient: A (0,1% TFA in H2O)
B (0,1% TFA in Methanol)
Min. 0-5 (100%A), Min. 5-35(0-50% B)

LSEQDEE
NO:1
RUN ON SEP-20-84    15:51

FLOW RATE    : 1,0
FLOW MODE    : QG
TEMPERATURE  : 40
PRESSURE     : 0070
COLUMN       : HD-SIL-18-5S-100

CHAN1: 220
MOBILE PHASE FILE 4

| TIME | %A | %B |
|---|---|---|
| 0.0 | 100.0 | 0.0 |
| 5.0 | 100.0 | 0.0 |
| 35.0 | 50.0 | 50.0 |
| 40.0 | 100.0 | 0.0 |

SEP-20-84   15:51

CHANNE 1   RUN 61   FILE 1   METHOD 0
INDEX 23

| PEAK | AREA% | RT | AREA |
|---|---|---|---|
| 1 | 3,094 | 224 | 3168 |
| 2 | 6,329 | 233 | 6482 |
| 3 | 1,799 | 245 | 1843 |
| 4 | 87,02 | 259 | 89123 |
| 5 | 1,758 | 285 | 1800 |
| TOTALS | 99,98 | | 102416 |

CARDIODILATIN - Fragment
(78-84)
Retention time: 24,5 Min.
Gradient : A (0,1% TFA in H₂O)
B (0,1% TFA in Methanol)
Min. 0-5 (100%A), Min. 5-50 (0-50% B)

INJECT  13:21:37

END OF RUN  14:11:39

IPSDRSA
NO:1
RUN ON DEC-28-84  13:21

FLOW RATE : 1.0
FLOW MODE : QG
PRESSURE : 0082
COLUMN : HD-SIL-18-5S-100N
CHAN 1 : 230
MOBILE PHASE FILE 4

| TIME | %A | %B |
|------|------|------|
| 0.0 | 100.0 | 0.0 |
| 5.0 | 100.0 | 0.0 |
| 40.0 | 50.0 | 50.0 |

END OF PROGRAMMED RUN

| PEAK | AREA% | RT | AREA |
|------|-------|-----|--------|
| 1 | 8,606 | 202 | 19405 |
| 2 | 1,644 | 224 | 3707 |
| 3 | 16,37 | 234 | 36910 |
| 4 | 46,91 | 245 | 105771 |
| 5 | 12,32 | 253 | 27781 |
| 6 | 1,585 | 394 | 3575 |
| 7 | 12,57 | 489 | 28342 |
| TOTALS | 99,99 | | 225491 |

INJECT 14:45:30 1

246
270

END OF RUN 15:35:32

PRSLRRSS
NO: 1
RUN ON DEC-15-84 14:45
FLOW RATE : 1,0
FLOW MODE: QG
PRESSURE : 0116
COLUMN : HD-SIL-18-5S-100N
CHAN 1 : 230
MOBILE PHASE FILE 4
TIME  %A     %B
 0.0  100.0   0.0
 5.0  100.0   0.0
40.0   50.0  50.0

END OF PROGRAMMED RUN

CARDIODILATIN-Fragment
(96-104)
Retention time: 27,8 Min.
 radient : A (0,1% TFA in H2O),
           B (0,1% TFA in Methanol)
Min. 0-5(100%A), Min. 5-50 (0-50%B)

| PEAK | AREA % | RT | AREA |
|---|---|---|---|
| 1 | 100 | 270 | 57862 |
| TOTALS | 100 | | 57862 |

CARDIODILATIN-Fragment
(108-114) Variant Tyr (Pos.107)
cyclic form
Retention time: 34,9 Min.
Gradient: A (0,1% TFA in H$_2$O)
B (0,1% TFA in Methanol)
Min. 0-5 (100%A), Min. 5-35 (0-50%B)

END OF RUN 10:16:23

CYCLO-YGRMDRIG
NO: 1
RUN ON SEP-25-84 09:36

FLOW RATE : 1.0
FLOW MODE : QG
TEMPERATURE : 40
PRESSURE : 0070
COLUMN : HD-SIL-18-10-100

CHAN 1 : 230
MOBILE PHASE FILE 4

| TIME | %A | %B |
|------|------|------|
| 0.0 | 100.0 | 0.0 |
| 5.0 | 100.0 | 0.0 |
| 35.0 | 50.0 | 50.0 |
| 40.0 | 100.0 | 0.0 |

| PEAK | AREA % | RT | AREA |
|------|--------|-----|--------|
| 1 | 1.123 | 205 | 1557 |
| 2 | 6.114 | 265 | 8475 |
| 3 | 92.76 | 349 | 128581 |
| TOTALS | 99.99 | | 138613 |

CARDIODILATIN, A NEW PEPTIDE HORMONE AND PROCESS FOR ITS PREPARATION

DESCRIPTION

The invention concerns a new peptide hormone and a process for its preparation.

From electron microscopic investigations, it was known that the right heart auricle (atrium) of the pig contains two different cell types, one of which has the morphology of endocrine cells (secretary granular). By means of morphological and histological investigations of the right atrium, however, no hormone substance, such as that of the type already known in myoendocrine cells of the heart auricle, could be determined. On the other hand, many of the known neuropeptide hormones were ascertained in the heart nerves.

It has now been found that atrium extracts (heart auricle), besides an already described diuretic activity (cf. J. -P. Marie, H. Guillemont, P. Y. Hatt, *Pathol. Biol.*, 24 (1976) (549–554), surprisingly display effects on the ionotropia of the heart muscle itself or influences on the smooth blood vessel musculature, as well as influences on the secretion of perspiration. Furthermore, it was found that these biological actions were caused by a new peptide hormone which, having regard to its actions, has a great clinical and therapeutic importance, especially with regard to the diagnosis and therapy of hypertonia.

Therefore, the subject of the invention is the new peptide hormone cardiodilatin with the N-terminal amino acid sequence: Asn-Pro-Val-Tyr-Gly-Ser-Val-Ser-Asn-Ala-Asp-Leu-Met-Asp-Phe-Lys-Asn-Leu-Leu-Asp-His-Leu-Glu-Asp-Lys-Met-Pro-Leu-Glu-Asp-Glu-Ala-Met-Pro-Pro-Gln-Val-Leu-Ser-Glu-Gln-Asp-Glu-Glu-Val-Gly-Ala-Pro-Leu-Pro-Leu-Leu-Glu-Glu-Val-Pro-Pro-Trp-Thr-Gly-Glu-Val-Asn-Pr of the composition: Asp/Asn 14, Thr 3, Ser 15, Glu/Glu 12, Pro 10, Gly 12, Ala 10, Val 7, Met 4, Ile 1, Leu 15, Tyr 2, Phe 3, Lys 4, His 2, Arg 10, Trp 2, a length of 126 amino acid residues and an isoelectric point I.P. of 6 to 6.5.

Furthermore, it has been found that fragments, especially C-terminal fragments and the fragments of the peptide hormone cardiodilatin present between two Met residues of the peptide chain display the biological activities of cardiodilatin, even though, in part, in weakened form.

Therefore, the subject of the invention are also the fragments of the peptide hormone cardiodilatin present between two Met residues of the peptide chain, such as e.g. the fragment with the amino acid sequence Asp-Phe-Lys-Asn-Leu-Leu-Asp-His-Leu-Glu-Asp-Lys-Hse (1) or the fragment with the amino acid sequence Pro-Leu-Glu-Asp-Glu-Ala-Hse (2) and the N-terminal fragment Asn-Pro-Val-Tyr-Gly-Ser-Val-Ser-Asn-Ala-Asp-Leu-Hse, as well as in each case the C-terminal remaining rump sequence of the cardiodilatin 126 shortened by the state homoserine peptides. One obtains these fragments by partial cyanogen bromide fissions, whereby the N-terminal shortening of the cardiodilatin leads to separated off fragments which, in each case, end C-terminally with homoserine (Hse). The N-terminal shortened fragments of cardiodilatin formed by fission with arginine-specific endopeptidase also display qualitatively the same biological effectiveness as the parent molecule even though in weakened form.

Furthermore, a series of cardiodilation fragments were prepared either synthetically by Merrifield synthesis or by fission of the cardiodilatin with specifically-splitting proteases and investigated. The Merrifield synthesis was thereby so carried out that, beginning at the C-terminal end, the amino acid chain was, in each case, lengthened by two amino acids, split off, investigated and, according to the same principle, lengthened by a further two amino acids. This process was repeated as often as was necessary for the fragments obtained and more closely defined further below.

The fragments prepared display an interesting biological activity, namely, they are suitable for the formation of antibodies which are able to recognise the whole cardiodilatin and, therefore, can also be used for its detection in the scope of an immune assay. There are suitable not only the numerous known embodimental forms of the RIA (radio-immune assay) but also of the EIA (enzyme immune assay). Furthermore, it was shown that some of the fragments also display the vasodilatory effectiveness of cardiodilatin, especially the fragment containing the amino acids 39 to 126 and the corresponding fragments lengthened N-terminally up to amino acid 7.

Therefore, a further subject of the invention are the following stated fragments, which are characterised by the HPLC data:

Fragments which include the amino acid positions 1 to 7: Asn-Pro-Val-Tyr-Gly-Ser-Val, as well as its structure variation Met (position 3), Asn (position 5) and Ala (position 6), both also N-terminally lengthened by the sequence Lys-Lys; e.g. Lys-Lys-Asn-Pro-Val-Tyr-Gly-Ser-Val.

Fragment 8 to 19: Ser-Asn-Ala-Asp-Leu-Met-Asp-Phe-Lys-Asn-Leu-Leu (see FIG. 3)

Fragment 23 to 28: Glu-Asp-Lys-Met-Pro-Leu, as well as its structure variation Glu (position 24) (see FIG. 4).

Fragment 29 to 37: Glu-Asp-Glu-Ala-Met-Pro-Pro-Gln-Val, as well as its variants with Val (pos. 32 and 33) and Glu (pos. 37).

Fragment 38 to 44: Leu-Ser-Glu-Gln-Asp-Glu-Glu, as well as its variants with Pro (position 41), Asn (position 42). (FIG. 5).

Fragment 63 to 70: Asp-Pro-Ser-Gln-Arg-Asp-Gly-Gly, as well as its variants with Ser (position 63), Ala (position 65) (FIG. 6).

Fragment 73 to 79: Gly-Arg-Gly-Pro-Trp-Asp-Pro, as well as its variants wth Phe (position 77), Ser (position 79).

Fragment 78 to 84: Asp-Pro-Ser-Asp-Arg-Ser-Ala, as well as its variants with Ser (position 79) (FIG. 7).

Fragment 86 to 92: Leu-Lys-Ser-Lys-Leu-Arg-Ala.

Fragment 96 to 104: Gly-Pro-Arg-Ser-Leu-Arg-Arg-Ser-Ser, as well as its variants with Ala (position 96) (FIG. 8).

Fragment 108 to 114: with an additional Tyr (position 107), Tyr-Gly-Arg-Met-Asp-Arg-Ile, as well as its cyclic form

```
┌─────────────────────────────────────┐  (FIG. 9).
└─ Tyr—Glu—Arg—Met—Asp—Arg—Ile—Gly ─┘
```

Fragment 117 to 126: Ser-Gly-Leu-Gly-Cys-Asn-Ser-Phe-Arg-Tyr and its dimeric disulphide.

Fragment 120 to 126: Gly-Cys-Asn-Ser-Phe-Arg-Tyr and its dimeric disulphide.

Fragment 39 to 126: Ser-Glu-Gln-Asn-Glu-Glu-Val-Gly-Ala-Pro-Leu-Pro-Leu-Leu-Glu-Glu-Val-Pro-Pro-Trp-Thr-Gly-Glu-Val-Asp-Pro-Ser-Gln-Arg-Asp-Gly-Gly-Ala-Leu-Gly-Arg-Gly-Pro-Trp-Asp-Pro-Ser-Asp-Arg-Ser-Ala-Leu-Leu-Lys-Ser-Lys-Leu-Arg-Ala-Leu-Leu-Ala-Gly-Pro-Arg-Ser-Leu-Arg-Ar -Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr, as well as its structure variants in the region of the positions 39 to 65 Ser-Glu-Pro-Asn-Glu-Glu-Ala-Gly-Ala-Ala-Leu-Ser-Pro-Leu-Pro-Glu-Val-Pro-Pro-Trp-Thr-Gly-Glu-Val-Ser-Pro-Ala.

Figure 1:
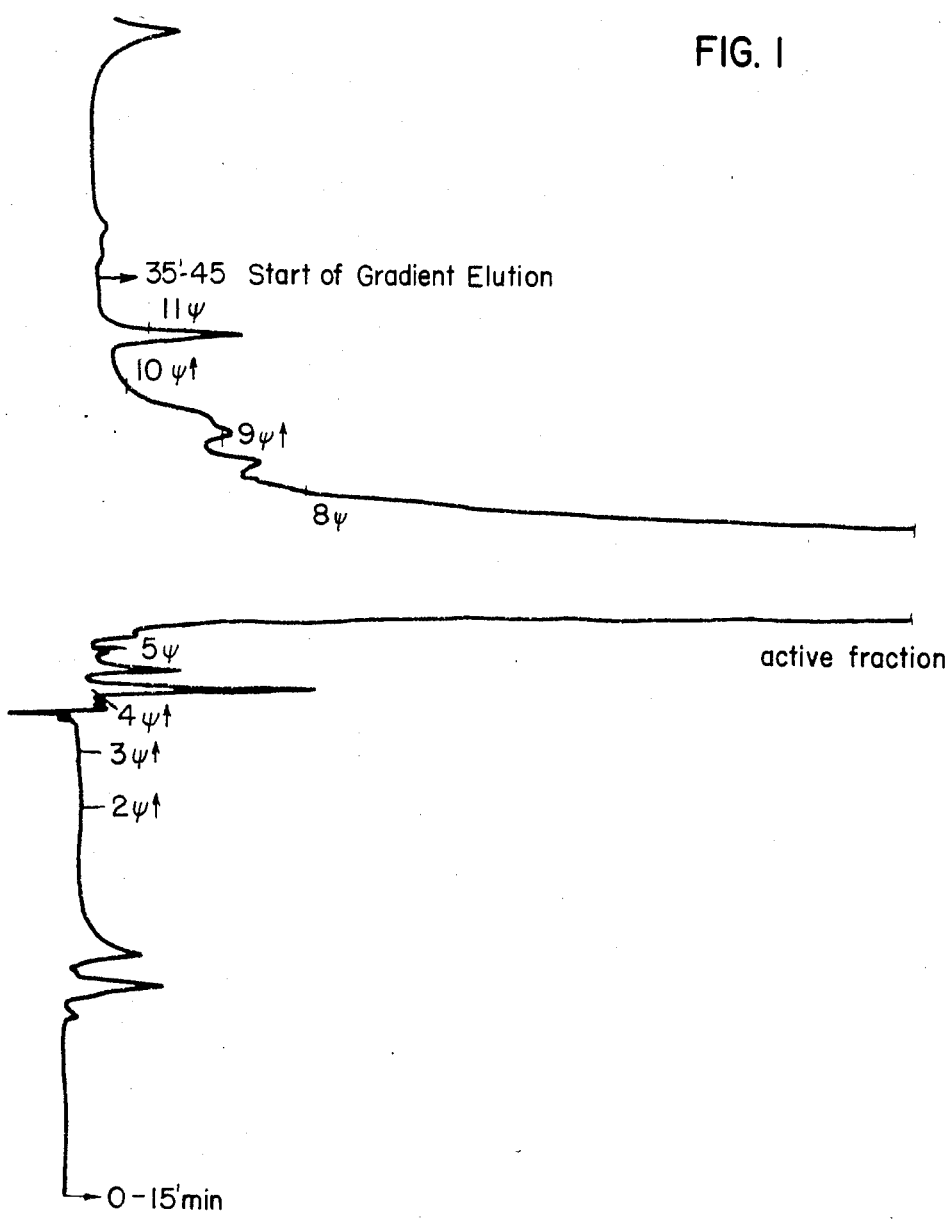
FIG. 1 shows a graphic illustration of the HPLC curve of the eluate of Example 2.
Figure 2:
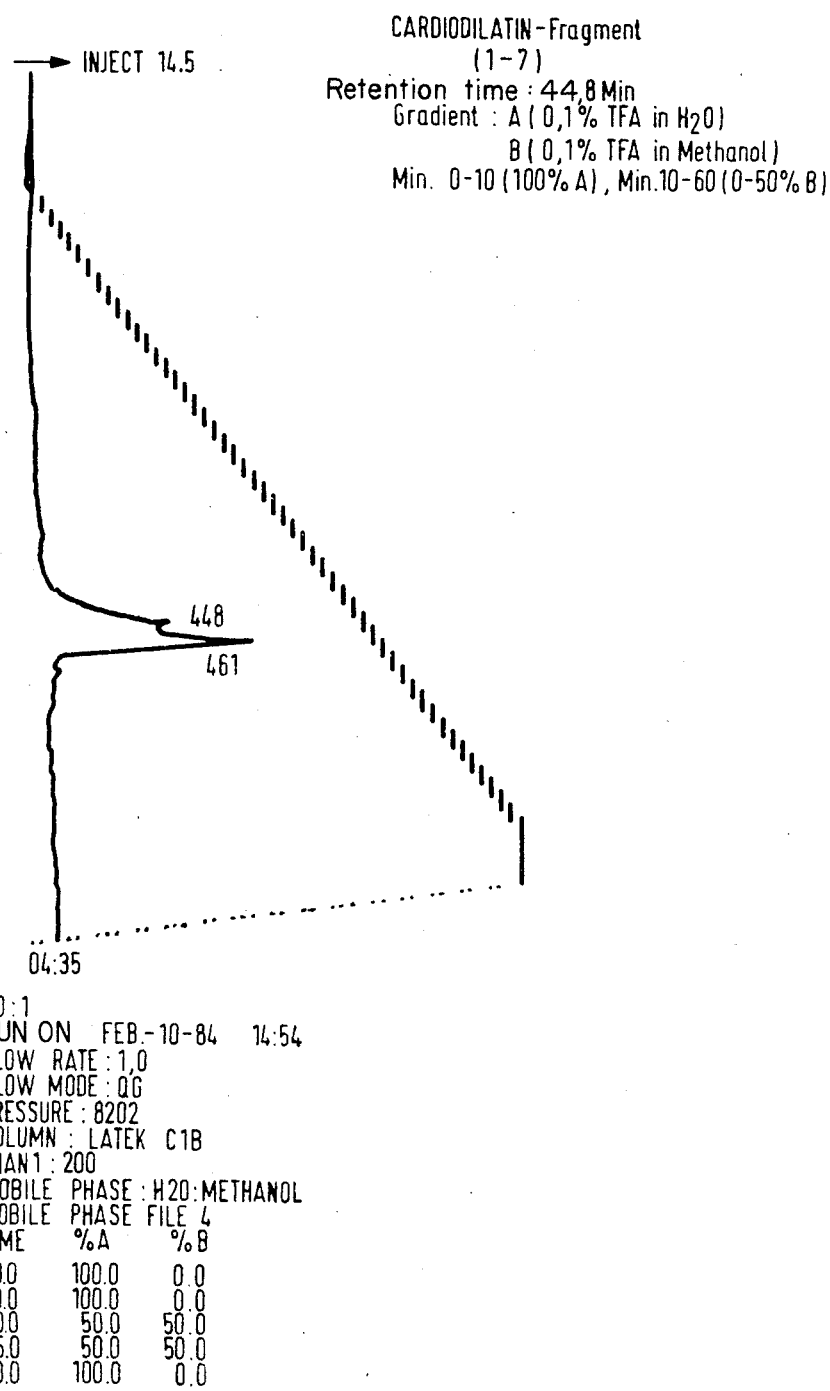
FIG. 2 shows a graphic illustration of the HPLC curve of cardiodilatin fragment (1–7).
Figure 2A:
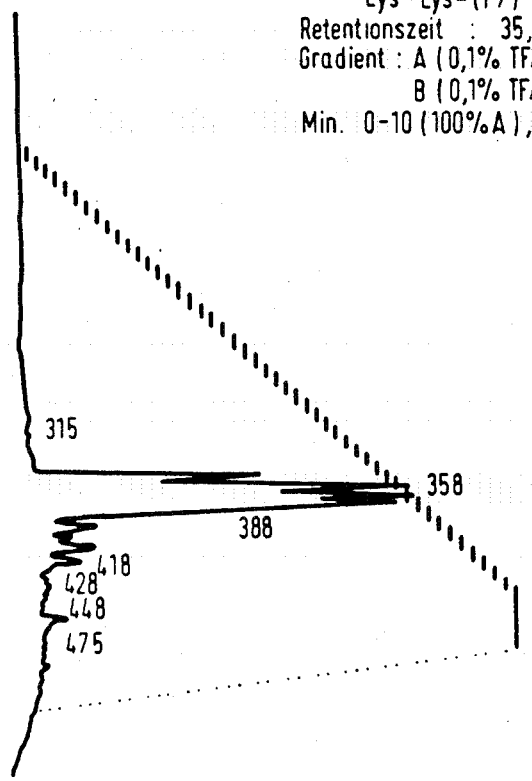
FIG. 2a shows a graphic illustration of the HPLC curve of cardiodilatin fragment Lys-Lys-(1–7).
Figure 2B:
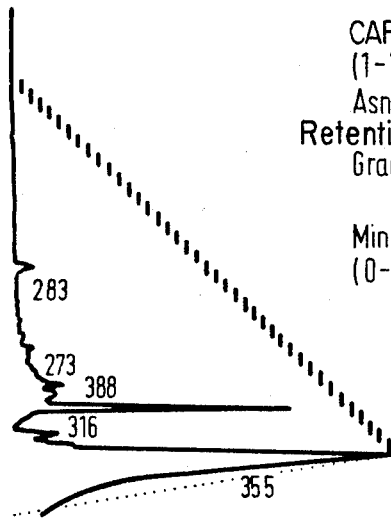
FIG. 2b shows a graphic illustration of the HPLC curve of cardiodilatin fragment (1–7), Met (Pos. 3), Asn (Pos. 5) and Ala (Pos. 6).
Figure 3:
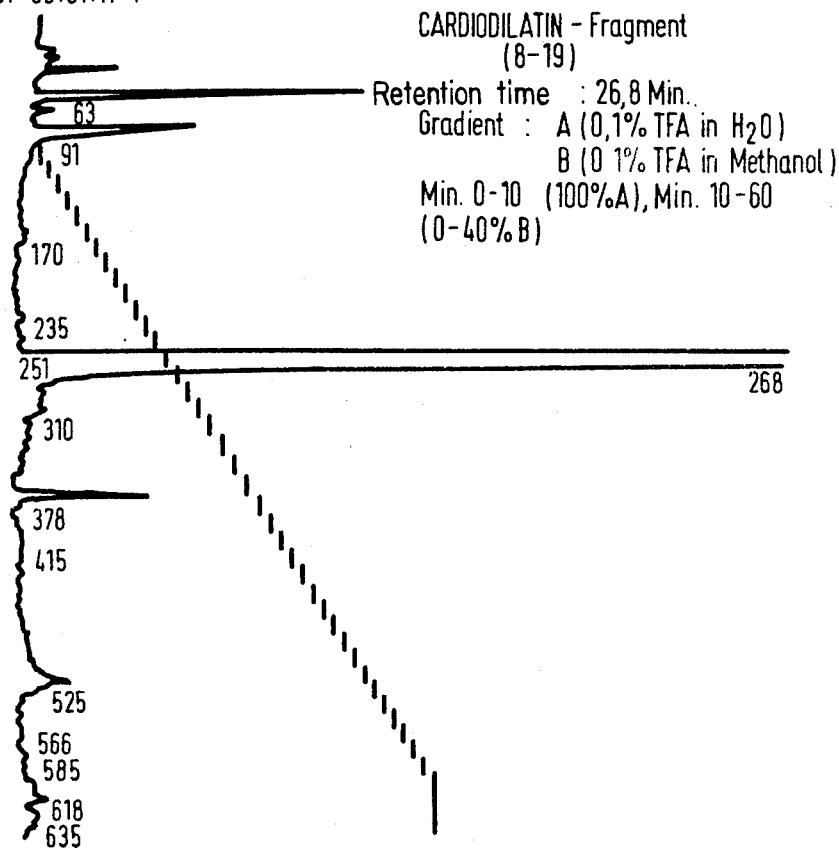
FIG. 3 shows a graphic illustration of the HPLC curve of cardiodilatin fragment (8–19).
Figure 4:
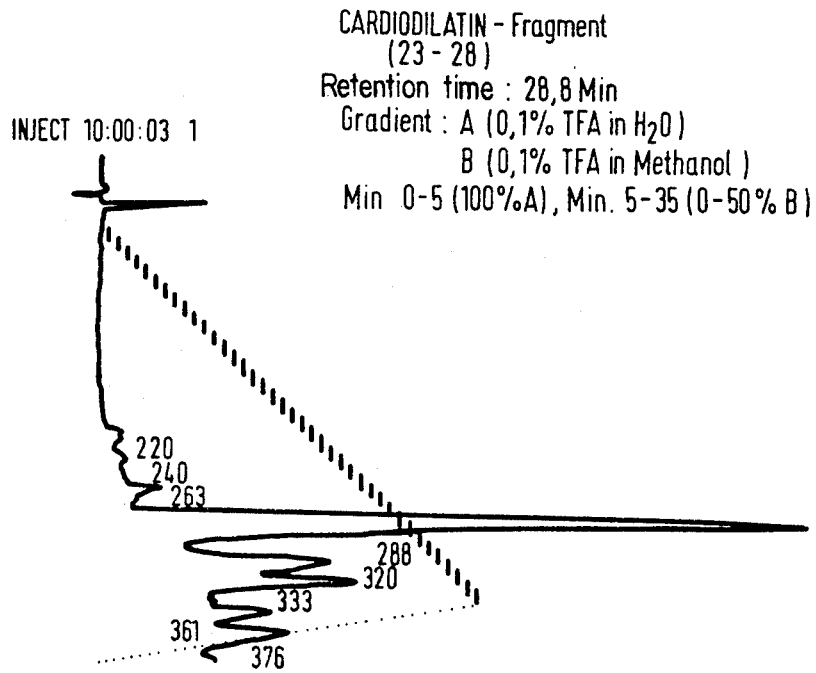
FIG. 4 shows a graphic illustration of the HPLC curve of cardiodilatin fragment (23–28).
Figure 5:
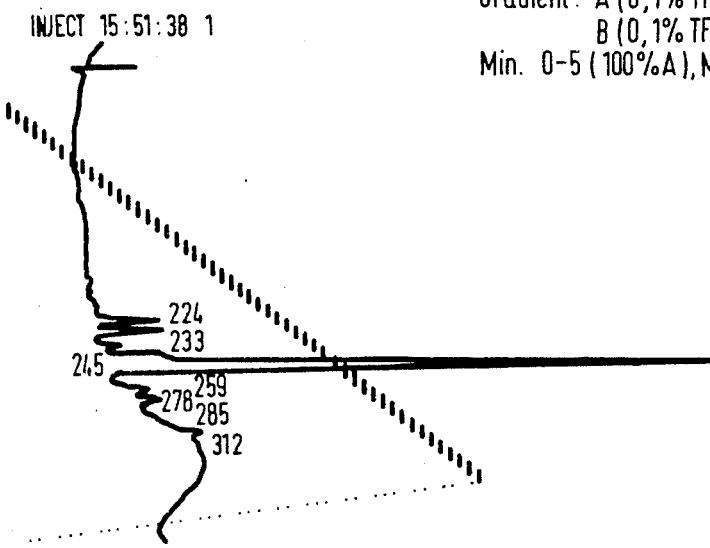
FIG. 5 shows a graphic illustration of the HPLC curve of cardiodilatin fragment (38–44).
Figure 6:
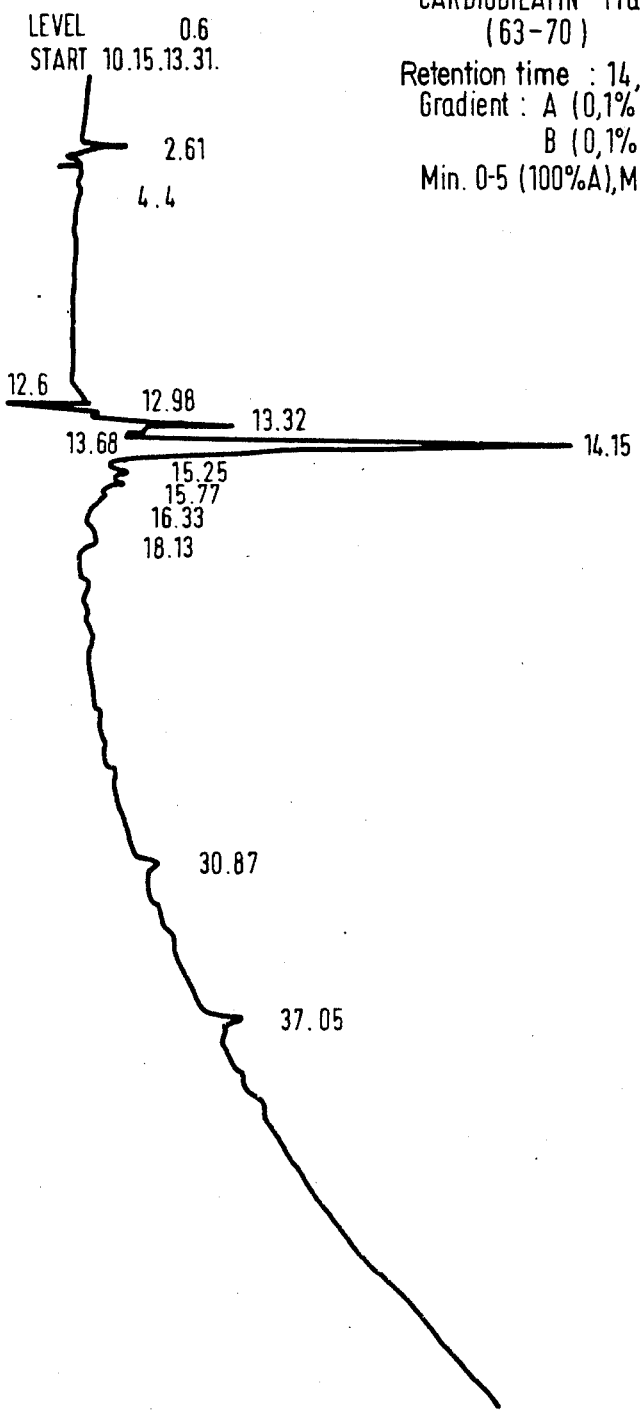
FIG. 6 shows a graphic illustration of the HPLC curve of cardiodilatin fragment (63–70).
Figure 7:
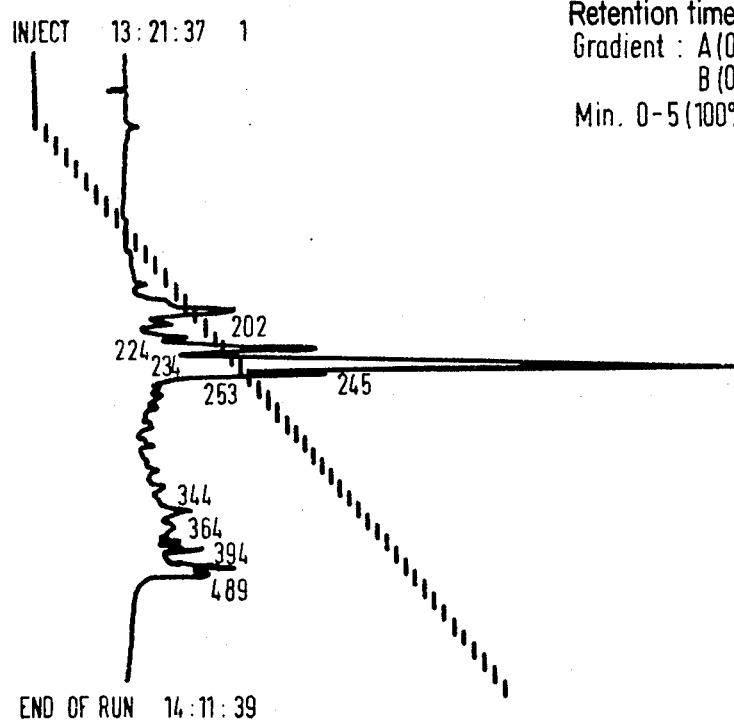
FIG. 7 shows a graphic illustration of the HPLC curve of cardiodilatin fragment (78–84).
Figure 8:
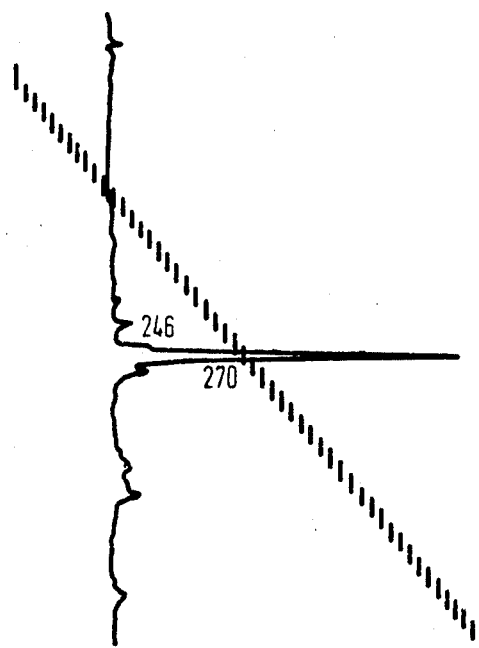
FIG. 8 shows a graphic illustration of the HPLC curve of cardiodilatin fragment (96–104).
Figure 9:
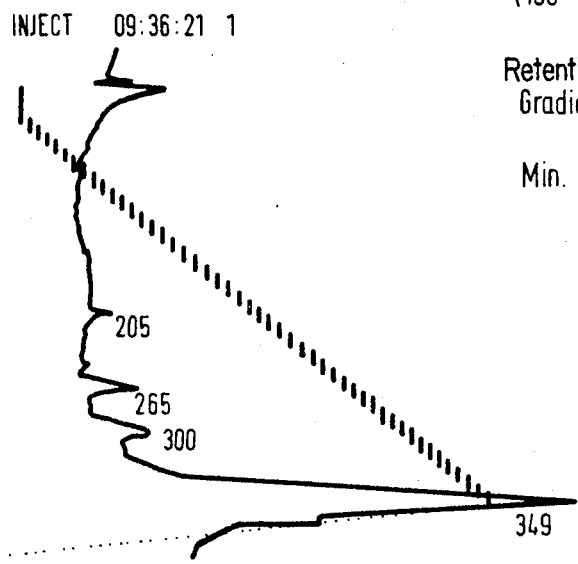
FIG. 9 shows a graphic illustration of the HPLC curve of cardiodilatin fragment (108–114), Tyr (Pos. 107).

In the case of N-terminal lengthening of the fragment 39 to 126 by one or more amino acids of the sequence 7 to 38 of the complete cardiodilatin in such a manner that a fragment always results which is identical in the sequence 7 to 126, one obtains fragments which also display the dilatory effectiveness of the complete cardiodilatin.

According to the invention, cardiodilatin is obtained in that one uses atrium extract as starting material and fractionates, according to usual biochemical purification methods, the material extractable with aqueous solvents with the use of a test in which the active fraction is determined by the relaxing action on smooth musculature. Preferably, the pure preparation of the peptide hormone cardiodilatin takes place from atrium extracts, e.g. of pig atria (V. Mutt, *Arkiv Kemi* 15, 69–74 (1959). Preferably, cardiodilatin is prepared in that one extracts boiled atrium material with dilute acid. As dilute acid, there are suitable, above all, the carboxylic acids but mineral acids can also be used. Preferably, one uses acetic acid, especially preferably in a concentration of 0.1 to 0.3M.

According to the invention, the further purification can so take place that one adsorbs the acid extract on alginic acid, again elutes the peptides with dilute mineral acid from the alginic acid, subjects the eluate to a salt precipitation, dissolves the precipitate thereby formed and again precipitates with ethanol. The ethanol precipitate is then dissolved and chromatographed over carboxymethylcellulose. A material so obtained is, as a rule, sufficiently pure for pharmaceutical or analytical purposes. The above-described precipitate obtained by salt precipitation can, alternatively, also be desalted directly and purified by gel chromatography, preferably on Sephadex G 25.

A fine purification is possible by means of high pressure liquid chromatography (HPLC) on a reverse phase silica gel (gradient elution: 0.1% trifluoroacetic acid in water against acetonitrile, 0 to 60%) and separation of the active fractions.

Expediently, the HPLC on a reverse phase silica gel is preceded by an HPLC on an ion exchanger column and/or the HPLC on reverse phase silica gel is repeated once or twice, preferably twice.

The N-terminal fragments, which are obtained either synthetically or by fission on the N-terminal methionine residue or arginine residue, bring about, after conjugation with a carrier protein, antibody formation in the case of administration to other animal types, such as rabbits or mice (Balb C), thus display hapten properties. These antibodies can be used as specific ligand in the affinity chromatography for the enrichment (isolation) and for the detection of the peptide hormone cardiodilatin. The affinity chromatography with an N-terminal fragment antibody as specific ligand thus represents a further suitable process for the enrichment (isolation) of the peptide hormone with which cardiodilatin can mostly already be obtained in sufficiently pure form. The affinity chromatography can also be employed with one of the above-mentioned chromatographic processes for the isolation of the peptide hormone or, however, one of the chromatographic methods can be followed by further purification according to one or more processes suitable therefor; suitable processes are e.g. electrophoresis, precipitation, adsorption chromatography, ion exchanger chromatography, affinity chromatography, isoelectric focussing or a combination of one or more identical or different ones of these steps.

The fragments present between two Met residues of the peptide chain can be prepared from the cardiodilatin in per se known manner by fission with suitable hydrolases but the fragments can also be prepared, such as e.g. the above-mentioned fragments with the amino sequence (1) and (2) or N-terminal fragments, by synthetic ways by per se known peptide syntheses, such as e.g. according to the method of Merrifield or synthesis with mixed anhydrides in solution.

As differentiating bioassay for the action of the peptide, there is used the relaxing effect in Arteria renalis (rabbit), Aorta abdominalis (rabbit, rat) and Arteria mesenterica inferior (rabbit) in an organ bath, whereby the blood vessel muscle strips contracted after adrenalin pretreatment show a distinct relaxation after the addition of cardiodilatin. This relaxation of the muscle strip from Arteria renalis is detectable after small doses of about 10 ng. to 100 ng./10 ml. of organ bath. In the case of strips of the aorta as test muscle, a detectable relaxation manifests itself at an about 10 times higher dosage, whereas on the Arteria mesenterica inferior of the rabbit, an activity was scarcely observed.

These biological actions show that the peptide hormone cardiodilatin and, as has been found, also its fragments, especially the C-terminal ones which stand after or between Met residues and can be obtained by partial cyanogen bromide fission, possess a great clinical (diagnostic) and therapeutic importance, namely, especially with regard to:

1. Differentiated vasodilation of certain beds of blood vessels,
2. diagnosis of hypertonia,
3. therapy of hypertonia,
4. possibility of diagnosing auricular dilations on the basis of the liberation of the hormone, and
5. use of this peptide hormone as substitution in the case of patients to whom artificial hearts have been implanted.
6. Furthermore, a synchronic regulation of the blood volume and of the blood electrolytes is conjectured on which the peptide has influence.
7. Skin diseases, especially with disturbance of the secretion of perspiration,
8. cardiovascular shock,
9. diseases of the kidney and adrenal cortex,
10. diseases of the digestive tract, especially of motility disturbances.

The subject of the invention are, therefore, also medicaments for use in the case of the above-stated diagnostic and therapy processes which contain the new peptide hormone cardiodilatin and/or active fragments thereof. The medicaments can be present in the usual forms of administration for oral or parenteral administration, such as e.g. as tablets, suppositories, dragees, solutions etc., possibly together with usual, pharmacologically acceptable carrier and/or dilution agents. The amount of cardiodilatin preferably amounts to 10 to 1000 ng./dosage unit.

EXAMPLE 1

With the use of conventional electron-microscopic methods, those places were determined in the right atrium of pigs' hearts which display the highest density of myoendocrine cells (endocrine secretion grannular). These cells were mainly found on the thin-walled places of the auricle. Having regard to their size distribution (230 and 50 nm.) and their electron density, these pig granula are comparable with the human granula; the number of the granula amounts to about 0.02 to 0.04 granula/$\mu m^2$ of the cut surface.

This above-described tissue of the right atrium was removed from 20,000 pig hearts and extracted according to known processes (cf. V. Mutt, Arkiv Kemi 15, 69–74 (1959), S. I. Said and V. Mutt, Eur. J. Biochem. 28, 199–204 (1972), V. Mutt, Gut hormones, pp 21–27, S. R. Bloom/editor), Edinburgh-London-New York: Churchill Livingstone, 1978).

EXAMPLE 2

For this purpose, 40 kg. of pig atrium was boiled and extracted with 0.2M acetic acid. The filtrate was adsorbed on alginic acid, the alginic acid washed with ethanol and subsequently eluted with 0.2M hydrochloric acid. The eluate containing the peptides is then mixed with salt until the peptides precipitate out and the precipitate centrifuged off. The precipitate is again dissolved in phosphate buffer, pH 7, and again precipitated by the addition of ethanol. The precipitate was again dissolved in phosphate buffer, pH 6.4, and applied to a carboxymethylcellulose. The column had been previously equilibrated with a buffer containing 0.03M NaOH, 0.025M $H_3PO_4$, 0.5% thiodiglycol, pH 6.4. After elution with the same buffer, there took place a further elution with a buffer containing 0.03M NaOH, 0.025M $H_3PO_4$ and 0.2M NaCl, pH 6.4. The most active fractions were hereby eluted.

The fraction eluted with the sale-containing buffer is applied to an ion exchanger column (TSK carboxymethylcellulose of the Firm LKB) and eluted with 0.03M sodium phosphate buffer, pH 6.4, and a sodium chloride gradient of 0 to 0.5M. The active fraction is collected, desalted over a molecular sieve (Sephadex G 25 ®) and subjected to preparative high pressure liquid chromatography (HPLC) with reversed phase, preferably with the use of an Organogen $C_{18}$-5$\mu$ ® column.

column: Waters $C_{18}$-$\mu$ Bondapak, 4×250 nm.

gradient elution: 0.1% trifluoroacetic acid in water against acetonitrile, 0 to 60% in 45 minutes.

The peptide cardiodilatin emerges at 45% acetonitrile from the HPLC column and displays a retention time of 24.1 minutes.

FIG. 1 shows a graphic illustration of this HPLC.

The active fraction obtained was thereafter again subjected twice to the same HPLC.

The isoelectric point I.P. was determined with 6 to 6.5.

The peptide showed, in the amino acid analysis, the following composition: Asp/Asn 14, Thr 3, Ser 15, Glu/Gln 12, Pro 10, Gly 12, Ala 10, Val 7, Met 4, Ile 1, Leu 15, Tyr 2, Phe 3, Lys 4, His 2, Arg 10, Trp 2.

The amino acid sequence was determined, starting from the N-terminus, by automated Edman breakdown, as follows: Asn-Pro-Val-Tyr-Gly-Ser-Val-Ser-Asn-Ala-Asp-Leu-Met-Asp-Phe-Lys-Asn-Leu-Leu-Asp-His-Leu-Glu-Asp-Lys-Met-Pro-Leu-Glu-Asp-Glu-Ala-Met-Pro-Pro-Gln-Val-Leu-Ser-Glu-Gln-Asp-Glu-Glu-Val-Gly-Ala-Pro-Leu-Pro-Leu-Leu-Glu-Glu-Val-Pro-Pro-Trp-Thr-Gly-Glu-Val-Asn-Pr (according to the sequence analysis, the whole sequence included 126 amino acid residues).

On the basis of the amino acid composition, there is calculated a molecular weight of about 13000 Dalton.

For the various stages of the purification process, biological tests were carried out according to the following bioassay, whereby, with progressive degree of purification, an increase of the specific activity was shown.

Carrying out of the bioassay:

Bioassays were carried out on smooth musculature in which was determined the relaxation in an organ bath due to the action of the fractions to be tested.

I claim:
1. Substantially pure peptide hormone cardiodilatin, characterized by an isoelectric point of from about 6 to about 6.5, an amino acid content of 14 Asp/Asn, 3 Thr, 15 Ser, 12 Glu/Gln, 10 Pro, 12 Gly, 10 Ala, 7 Val, 4 Met, 1 Ile, 15 Leu, 2 Tyr, 3 Phe, 4 Lys, 2 His, 10 Arg, and 2 Trp, and N-terminal amino acid sequence: Asn-Pro-Val-Tyr-Gly-Ser-Val-Ser-Asn-Ala-Asp-Leu-Met-Asp-Phe-Lys-Asn-Leu-Leu-Asp-His-Leu-Glu-Asp-Lys-Met-Pro-Leu-Glu-Asp-Glu-Ala-Met-Pro-Pro-Gln-Val-Leu-Ser-Glu-Gln-Asp-Glu-Glu-Val-Gly-Ala-Pro-Leu-Pro-Leu-Leu-Glu-Glu-Val-Pro-Pro-Trp-Thr-Gly-Glu-Val-Asn-Pr.

2. Biologically active fragments of cardiodilatin of claim 1.

3. Fragments of claim 2, wherein said fragments terminate at, but do not include, a Met or Arg residue at at least one end.

4. Fragments of claim 3, wherein said fragments have a C-terminal homoserine group added thereto.

5. Fragments of claim 4, with amino acid sequence Asp-Phe-Lys-Asn-Leu-Leu-Asp-His-Leu-Glu-X Lys-Hse, wherein X is Glu or Asp.

6. Fragments of claim 4, with amino acid sequence Pro-Leu-Glu-Asp-Glu-Ala-Hse.

7. Fragments of claim 4, wherein said fragments are N-terminal fragments with amino acid sequence Asn-Pro-A-Tyr-B-C-Val-Ser-Asn-Ala-Asp-Leu-Hse, where A is Val or Met, and if A is Val, B is Gly and C is Ser, and if A is Met, B is Asn and C is Ala.

8. Fragments of claim 2, obtained by action of arginine specific endopeptidase.

9. Fragments of claim 2, having amino acid sequence Asn-Pro-A-Tyr-B-C-Val, wherein A is Val or Met, and if A is Val, B is Gly and C is Ser, and if A is Met, B is Asn and C is Ala.

10. Fragments of claim 9, wherein two N-terminal Lys residues are added thereto.

11. Fragments of claim 2, having amino acid sequence Glu-Asp-Lys-Met-Pro-Leu.

12. Fragments of claim 2, having amino acid sequence Glu-Asp-Glu-A-B-Pro-Pro-Glyn-Val, where A is Ala or Val, and if A is Ala, B is Met, and if A is Val, B is Val.

13. Fragments of claim 2, with amino acid sequence Leu-Ser-Glu-A-B-Glu-Glu where A is Gln or Pro, and if A is Gln, B is Asp, and if A is Pro, B is Asn.

14. Fragments of claim 2, with amino acid sequence A-Pro-B-Gln-Arg-Asp-Gly-Gly, where A is Ser or Asp, and if A is Ser, B is Ala, and if A is Asp, B is Ser.

15. Fragments of claim 2, with amino acid sequence Gly-Arg-Gly-Pro-A-Asp-B-Ser, where A is Trp or Phe, and B is Pro or Ser.

16. Fragments of claim 2, with amino acid sequence Ser-Asp-A-Ser-Asp-Arg-Ser-Ala, where A is Pro or Ser.

17. Fragments of claim 2 with amino acid sequence Leu-Lys-Ser-Lys-Leu-Aug-Ala.

18. Fragments of claim 5, with amino acid sequence A-Pro-Arg-Ser-Leu-Arg-Arg-Ser-Ser wherein A is Gly or Ala.

19. Fragments of claim 2, with amino acid sequence Tyr-Gly-Arg-Met-Asp-Arg-Ile-Gly-A, wherein A is hydrazide or a bond between terminal Tyr and terminal Gly.

20. Fragments of claim 2, with amino acid sequence Ser-Gly-Leu-Gly-Cys-Asn-Ser-Phe-Arg-Tyr.

21. Fragments of claim 2, wherein said fragments are dimeric disulfides of fragment Ser-Gly-Leu-Gly-Cys-Asn-Ser-Phe-Arg-Tyr.

22. Fragments of claim 2, with amino acid sequence Gly-Cys-Asn-Ser-Phe-Arg-Tyr.

23. Fragments of claim 2, wherein said fragments are dimeric disulfides of fragment Gly-Cys-Asn-Ser-Phe-Arg-Tyr.

24. Fragments of claim 2, with amino acid sequence Ser-Glu-Gln-Asn-Glu-Glu-Val-Gly-Ala-Pro-Leu-Pro-Leu-Leu-Glu-Glu-Val-Pro-Pro-Trp-Tyr-Gly-Glu-Val-Asn-Pro.

25. Fragments of claim 2, with amino acid sequence: Ser-Glu-Pro-Asn-Glu-Glu-Ala-Gly-Ala-Ala-Leu-Ser-Pro-Leu-Pro-Glu-Val-Pro-Pro-Trp-Thr-Gly-Glu-Val-Ser-Pro-Ala-Gln-Arg-Asp-Gly-Gly-Ala-Leu-Gly-Arg-Gly-Pro-Trp-Asp-Ser-Ser-Asp-Arg-Ser-Ala-Leu-Leu-Lys-Ser-Lys-Leu-Arg-Ala-Leu-Leu-Thr-Ala-Pro-Arg-Ser-Leu-Arg-Arg Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr.

26. Fragments of claim 25, wherein the sequence Val-Ser-Asn-Ala-Asp-Leu-Met-Asp-Phe-Lys-Asn-Leu-Leu-Asp-His-Leu-Glu-A-B-Met-Pro-Leu-Glu-Asp-Glu-C-D-Pro-Pro-Gln-Val-Leu-Ser, or a C-terminal fraction thereof is added to the Tyr end of said fragment wherein A is Asp, Glu, or Val, if A is Asp or Glu, B is Lys, if A is Val, B is Val, C is Ala, Glu or Val, and if C is Ala, D is Met, if C is Glu, D is Lys, and if C is Val, D is Val.

27. Fragments of claim 2, having amino acid sequence Ser-Asn-Ala-Asp-Leu-Met-Asp-Phe-Lys-Asn-Leu-Leu.

28. Fragment of claim 2, wherein said fragment has amino acid sequence Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr.

29. Substantially pure peptide hormone cardiodilatin, having amino acid sequence: Asn-Pro-Val-Tyr-Gly-Ser-Val-Ser-Asn-Ala-Asp-Leu-Met-Asp-Phe-Lys-Asn-Leu-Leu-Asp-His-Leu-Glu-Asp-Lys-Met-Pro-Leu-Glu-Asp-Glu-Ala-Met-Pro-Pro-Gln-Val-Leu-Ser-Glu-Gln-Asn-Glu-Glu-Val-Gly-Ala-Pro-Leu-Ser-Pro-Leu-Leu-Glu-Val-Pro-Pro-Trp-Thr-Gly-Glu-Val-Asn-Pr-Ala-Gln-Arg-Asp-Gly-Gly-Ala-Leu-Gly-Arg-Gly-Pro-Trp-Asp-Ala-Ser-Asp-Arg-Ser-Ala-Leu-Leu-Lys-Ser-Lys-Leu-Arg-Ala-Leu-Leu-Ala-Ala-Pro-Arg-Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe Arg-Tyr-OH and fragments thereof.

30. Substantially pure peptide hormone cardiodilatin having amino acid sequence: Asn-Pro-Val-Tyr-Gly-Ser-Val-Ser-Asn-Ala-Asp-Leu-Met-Asp-Phe-Lys-Asn-Leu-Leu-Asp-His-Leu-Glu-Asp-Lys-Met-Pro-Leu-Glu-Asp-Glu-Ala-Met-Pro-Pro-Gln-Val-Leu-Ser-Glu-Gln-Asn-Glu-Glu-Val-Gly-Ala-Pro-Leu-Pro-Leu-Leu-Glu-Glu-Val-Pro-Pro-Trp-Thr-Gly-Glu-Val-Asn-Pr-Ala-Gln-Arg-Asp-Gly-Gly-Ala-Leu-Gly-Arg-Gly-Pro-Trp-Asp-Ala-Ser-Asp-Arg-Ser-Ala-Leu-Leu-Lys-Ser-Lys-Leu-Arg-Ala-Leu-Leu-Ala-Ala-Pro-Arg-Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr-OH and fragments thereof.

* * * * *

UNITED STATES PATENT AND TRADEMARK OFFICE
CERTIFICATE OF CORRECTION

PATENT NO. : 4,751,284

DATED : June 14, 1988

INVENTOR(S) : Wolf-Georg Forssmann

It is certified that error appears in the above-identified patent and that said Letters Patent is hereby corrected as shown below:

On the Title Page, in the Abstract, line 9,
    change "A n" to -- Asn --.

Column 1, line 38: change "Pr" to -- Pro --;
          line 39: change "Glu/Glu" to -- Glu/Gln --.

Column 3, line 6: change "Ar" to -- Arg --;
Column 6, line 32: change "Pr" to -- Pro --.

Column 6, line 58: change "Pr" to -- Pro --.

Column 8, line 34: change "Pr" to -- Pro --;
          line 47: change "Pr" to -- Pro --.

Signed and Sealed this

Twenty-first Day of March, 1989

*Attest:*

DONALD J. QUIGG

*Attesting Officer*    *Commissioner of Patents and Trademarks*